United States Patent
Hammon et al.

(10) Patent No.: US 10,493,376 B2
(45) Date of Patent: Dec. 3, 2019

(54) COLUMN FOR THERMAL TREATMENT OF FLUID MIXTURES

(71) Applicant: BASF SE, Ludwigshafen am Rhein (DE)

(72) Inventors: Ulrich Hammon, Mannheim (DE); Thomas Walter, Hassloch (DE)

(73) Assignee: BASF SE, Ludwigshafen am Rhein (DE)

( * ) Notice: Subject to any disclaimer, the term of this patent is extended or adjusted under 35 U.S.C. 154(b) by 78 days.

(21) Appl. No.: 15/382,073

(22) Filed: Dec. 16, 2016

(65) Prior Publication Data
US 2017/0173492 A1    Jun. 22, 2017

Related U.S. Application Data

(60) Provisional application No. 62/269,118, filed on Dec. 18, 2015.

(30) Foreign Application Priority Data

Dec. 18, 2015    (DE) .................... 10 2015 122 209

(51) Int. Cl.
*B01D 3/32*    (2006.01)
*B01D 3/20*    (2006.01)
(Continued)

(52) U.S. Cl.
CPC .............. *B01D 3/324* (2013.01); *B01D 3/20* (2013.01); *B01D 3/205* (2013.01); *B01D 3/225* (2013.01);
(Continued)

(58) Field of Classification Search
CPC .......... B01D 3/324; B01D 3/26; B01D 53/18; B01D 3/225; B01D 3/20; B01D 3/32;
(Continued)

(56) References Cited

U.S. PATENT DOCUMENTS 2,366,360 A * 1/1945 Semon ..................... B01D 3/40
                                                                203/54
2,767,966 A * 10/1956 Chave ..................... B01D 3/18
                                                                261/113
(Continued)

FOREIGN PATENT DOCUMENTS

DE    197 40 252 A1    3/1999
DE    197 40 253 A1    3/1999
(Continued)

OTHER PUBLICATIONS

Helmuth Hausen, "Packungskolonnen", Chem.-Ing. Tech. 58 (1986) No. 1, pp. 19-31.

(Continued)

*Primary Examiner* — Stephen Hobson
(74) *Attorney, Agent, or Firm* — Oblon, McClelland, Maier & Neustadt, L.L.P.

(57) ABSTRACT

The present invention relates to a column (1) for thermal treatment of fluid mixtures, having a cylindrical, vertically aligned column body (2) which forms a column cavity (3), having a sequence of vertically spaced-apart dual-flow mass transfer trays (8) which are mounted in the column cavity (3) and which have orifices for passage of liquid and gas in countercurrent, and having at least one gas entry orifice (5) disposed below the lowermost of the sequence of dual-flow mass transfer trays (8). It is a characteristic feature of the column of the invention that a gas distribution tray (9) which is disposed between the lowermost of the sequence of dual-flow mass transfer trays (8) and the gas entry orifice (5) has orifices (32) for vertical passage of gas which can be introduced into the column cavity (3) via the gas entry orifice (5), the orifices (32) being formed so as to bring about equal gas distribution over the column cross section. The (Continued)

invention further relates to a process for thermal treatment of fluid mixtures in such a column (1).

13 Claims, 5 Drawing Sheets

(51) Int. Cl.
| | |
|---|---|
| C07C 51/42 | (2006.01) |
| C07C 51/44 | (2006.01) |
| B01D 3/22 | (2006.01) |
| B01D 3/26 | (2006.01) |
| B01D 53/18 | (2006.01) |
| C07C 67/52 | (2006.01) |

(52) U.S. Cl.
CPC .............. *B01D 3/26* (2013.01); *B01D 3/32* (2013.01); *B01D 53/18* (2013.01); *C07C 51/42* (2013.01); *C07C 51/44* (2013.01); *C07C 67/52* (2013.01)

(58) Field of Classification Search
CPC ......... B01D 3/205; C07C 67/52; C07C 51/44; C07C 51/42
See application file for complete search history.

(56) References Cited

U.S. PATENT DOCUMENTS

| | | | | |
|---|---|---|---|---|
| 3,412,016 | A * | 11/1968 | Graven | B01D 3/141 208/354 |
| 3,477,915 | A * | 11/1969 | Gantt | B01D 3/32 202/155 |
| 3,988,213 | A | 10/1976 | Yoshida et al. | |
| 4,309,396 | A * | 1/1982 | Herbrechtsmeier | C01B 21/40 423/235 |
| 4,426,361 | A * | 1/1984 | Bushnell | B01D 11/043 196/14.52 |
| 5,262,094 | A * | 11/1993 | Chuang | B01D 3/16 261/113 |
| 5,632,933 | A * | 5/1997 | Yeoman | B01D 3/32 261/109 |
| 5,739,391 | A | 4/1998 | Ruppel et al. | |
| 5,821,390 | A | 10/1998 | Ruppel et al. | |
| 6,448,439 | B1 | 9/2002 | Eck et al. | |
| 6,514,387 | B1 * | 2/2003 | Emmrich | B01D 3/141 196/111 |
| 6,646,161 | B1 | 11/2003 | Eck et al. | |
| 6,883,788 | B1 * | 4/2005 | Tagamolila | B01D 3/16 165/DIG. 197 |
| 7,235,158 | B2 * | 6/2007 | Matsumoto | B01D 3/22 202/158 |
| 7,520,964 | B2 * | 4/2009 | Hammon | B01D 3/22 202/158 |
| 7,909,966 | B2 * | 3/2011 | Wu | B01D 3/324 202/158 |
| 9,796,601 | B1 * | 10/2017 | Al-Qutub | C02F 1/048 |
| 2001/0007043 | A1 | 7/2001 | Machhammer et al. | |
| 2002/0043454 | A1 | 4/2002 | Machhammer et al. | |
| 2002/0163091 | A1 * | 11/2002 | Wu | B01D 3/163 261/114.4 |
| 2004/0073063 | A1 | 4/2004 | Thiel et al. | |
| 2004/0097756 | A1 | 5/2004 | Thiel et al. | |
| 2004/0249198 | A1 | 12/2004 | Thiel et al. | |
| 2005/0005418 | A1 | 1/2005 | Hammon et al. | |
| 2005/0211542 | A1 | 9/2005 | Hammon et al. | |
| 2005/0275121 | A1 * | 12/2005 | Burch | B01D 3/20 261/114.1 |
| 2006/0124431 | A1 * | 6/2006 | Xie | B01D 3/14 196/139 |
| 2008/0183014 | A1 | 7/2008 | Diefenbacher et al. | |
| 2011/0226607 | A1 * | 9/2011 | Anderson | B01D 3/32 203/84 |
| 2012/0103013 | A1 * | 5/2012 | King | B01D 3/141 62/625 |
| 2013/0118887 | A1 * | 5/2013 | Frolov | B01D 1/0047 202/185.1 |
| 2013/0220791 | A1 * | 8/2013 | Wakabayashi | B01D 3/007 202/154 |
| 2013/0256115 | A1 * | 10/2013 | Wakabayashi | B01D 1/28 202/154 |
| 2013/0274519 | A1 | 10/2013 | Mueller-Engel et al. | |
| 2014/0284824 | A1 * | 9/2014 | Bechtel | B01D 3/166 261/148 |
| 2015/0143845 | A1 * | 5/2015 | Wakabayashi | F25J 1/0022 62/630 |
| 2015/0343370 | A1 * | 12/2015 | Salu | B01D 53/263 95/11 |
| 2016/0206970 | A1 * | 7/2016 | Alzner | B01D 3/008 |
| 2016/0216051 | A1 * | 7/2016 | Kurukchi | F28F 25/10 |
| 2016/0288013 | A1 * | 10/2016 | Al-Qutub | C02F 1/048 |
| 2017/0340985 | A1 * | 11/2017 | Zhang | B01D 3/14 |

FOREIGN PATENT DOCUMENTS

| | | |
|---|---|---|
| DE | 199 24 532 A1 | 11/2000 |
| DE | 199 24 533 A1 | 11/2000 |
| DE | 101 56 988 A1 | 5/2003 |
| DE | 101 59 823 A1 | 6/2003 |
| DE | 102 18 419 A1 | 6/2003 |
| DE | 102 30 219 A1 | 1/2004 |
| DE | 103 36 386 A1 | 3/2004 |
| DE | 102 43 625 A1 | 4/2004 |
| DE | 103 32 758 A1 | 5/2004 |
| DE | 10 2010 001 228 A1 | 2/2011 |
| DE | 10 2012 204 436 A1 | 10/2012 |
| EP | 0 700 714 A1 | 3/1996 |
| EP | 0 700 893 A1 | 3/1996 |
| EP | 0 982 287 A1 | 3/2000 |
| EP | 0 982 289 A2 | 3/2000 |
| EP | 1 029 573 A2 | 8/2000 |
| EP | 1 125 912 A2 | 8/2001 |
| EP | 1 279 429 A1 | 1/2003 |
| WO | WO 2004/035514 A1 | 4/2004 |
| WO | WO 2008/090190 A1 | 7/2008 |

OTHER PUBLICATIONS

Technische Fortschrittsberichte [Technical Progress Reports], vol. 61, Grundlagen der Dimensionierung von Kolonnenböden [Fundamentals of the Dimensioning of Column Trays], Verlag Theodor Steinkopff, Dresden 1967, pp. 198 to 211 with cover pages.
W. Meier, Sulzer—Kolonnen für Rektifikation und Absorption, Technische Rundschau Sulzer Feb. 1979, pp. 49 ff. from Gebruder Sulzer Aktiengesellschaft in Winterthur, Switzerland.
U.S. Appl. No. 15/382,036, filed Dec. 16, 2016, Ulrich Hammon.
U.S. Appl. No. 14/817,351, filed Aug. 4, 2015, US 2016-0040929, Ulrich Hammon.
U.S. Appl. No. 14/816,485, filed Aug. 3, 2016, US 2016-0038852, Ulrich Hammon.
U.S. Appl. No. 14/573,313, filed Dec. 17, 2014, US 2016-0166455, Ulrich Hammon.
U.S. Appl. No. 14/857,998, filed Sep. 18, 2015, US 2016-0083267, Ulrich Hammon.
U.S. Appl. No. 14/661,462, filed Mar. 18, 2015, US 2015-0267391, Ulrich Hammon.
U.S. Appl. No. 14/661,408, filed Mar. 18, 2015, US 2015-0267967, Ulrich Hammon.
U.S. Appl. No. 14/738,033, filed Jun. 12, 2015, US 2015-0360142, Ulrich Hammon.
U.S. Appl. No. 14/738,050, filed Jun. 12, 2015, US 2016-0010850, Ulrich Hammon.
U.S. Appl. No. 14/737,025, filed Jun. 11, 2015, US 2015-0360191, Ulrich Hammon.
U.S. Appl. No. 14/857,967, filed Sep. 18, 2015, US 2016-0090347, Ulrich Hammon.
U.S. Appl. No. 17/659,753, filed Mar. 17, 2015, US 2015-0266000, Ulrich Hammon.

(56) References Cited

OTHER PUBLICATIONS

U.S. Appl. No. 14/633,433, filed Feb. 27, 2015, US 2015-0246343, Ulrich Hammon.
U.S. Appl. No. 15/072,463, filed Mar. 17, 2016, US 2016-0271516, Tim Blaschke.
International Preliminary Report on Patentability and Written Opinion dated Jun. 19, 2018 in PCT/EP2016/081561 (with English language translation).

* cited by examiner

COLUMN FOR THERMAL TREATMENT OF FLUID MIXTURES

The present invention relates to a column for thermal treatment of fluid mixtures. The column comprises a cylindrical, vertically aligned column body which forms a column cavity. In addition, the column has a sequence of vertically spaced-apart dual-flow mass transfer trays which are mounted in the column cavity and which have orifices for passage of liquid and gas in countercurrent. The column additionally comprises at least one gas entry orifice disposed below the lowermost of the sequence of dual-flow mass transfer trays. The invention further relates to a process for thermal treatment of fluid mixtures in a column.

In separation columns, gaseous (ascending) and liquid (descending) streams are in many cases conducted in countercurrent, at least one of the streams especially comprising a (meth)acrylic monomer. As a result of the inequilibria that exist between the streams, heat and mass transfer takes place, which ultimately causes the removal (or separation) desired in the separation column. In this document, such separation processes shall be referred to as thermal separation processes.

Examples of, and hence elements of, the expression "thermal separation processes" used in this document are fractional condensation (cf., for example, DE 19924532 A1, DE 10243625 A1 and WO 2008/090190 A1) and rectification (in both cases, ascending vapor phase is conducted in countercurrent to descending liquid phase; the separating action is based on the vapor composition at equilibrium being different from the liquid composition), absorption (at least one ascending gas is conducted in countercurrent to at least one descending liquid; the separating action is based on the different solubility of the gas constituents in the liquid) and desorption (the reverse process of absorption; the gas dissolved in the liquid phase is removed by lowering the partial pressure; if the partial pressure of the material dissolved in the liquid phase is lowered at least partly by passing a carrier gas through the liquid phase, this thermal separation process is also referred to as stripping; alternatively or additionally (simultaneously as a combination), the lowering of the partial pressure can also be brought about by lowering the working pressure).

For example, the removal of (meth)acrylic acid and/or (meth)acrolein from the product gas mixture of the catalytic gas phase oxidation can be conducted in such a way that the (meth)acrylic acid and/or the (meth)acrolein is first subjected to basic removal by absorption into a solvent (e.g. water or an organic solvent) or by fractional condensation of the product gas mixture, and the absorbate or condensate obtained is subsequently separated further to obtain (meth) acrylic acid and/or (meth)acrolein of greater or lesser purity (cf., for example, DE-10332758 A1, DE 10243625 A1, WO 2008/090190 A1, DE 10336386 A1, DE 19924532 A1, DE 19924533 A1, DE 102010001228 A1, WO 2004/035514 A1, EP 1125912 A2, EP 982289 A2, EP 982287 A1 and DE 10218419 A1).

The notation "(meth)acrylic monomers" in this document is an abbreviated form of "acrylic monomers and/or methacrylic monomers".

The term "acrylic monomers" in this document is an abbreviated form of "acrolein, acrylic acid and/or esters of acrylic acid".

The term "methacrylic monomers" in this document is an abbreviated form of "methacrolein, methacrylic acid and/or esters of methacrylic acid".

In particular, the (meth)acrylic monomers addressed in this document shall comprise the following (meth)acrylic esters: hydroxyethyl acrylate, hydroxyethyl methacrylate, hydroxypropyl acrylate, hydroxypropyl methacrylate, glycidyl acrylate, glycidyl methacrylate, methyl acrylate, methyl methacrylate, n-butyl acrylate, isobutyl acrylate, isobutyl methacrylate, n-butyl methacrylate, tert-butyl acrylate, tert-butyl methacrylate, ethyl acrylate, ethyl methacrylate, 2-ethylhexyl acrylate, 2-ethylhexyl methacrylate, N,N-dimethylaminoethyl acrylate and N,N-dimethylaminoethyl methacrylate.

(Meth)acrylic monomers are important starting compounds for preparation of polymers which find use, for example, as adhesives or as water-superabsorbing materials in hygiene articles.

On the industrial scale, (meth)acrolein and (meth)acrylic acid are prepared predominantly by catalytic gas phase oxidation of suitable $C_3/C_4$ precursor compounds (or of precursor compounds thereof). In the case of acrolein and acrylic acid, such precursor compounds used are preferably propene and propane. In the case of methacrylic acid and of methacrolein, isobutene and isobutane are the preferred precursor compounds.

As well as propene, propane, isobutene and isobutane, however, suitable starting materials are also other compounds comprising 3 or 4 carbon atoms, for example isobutanol, n-propanol or precursor compounds thereof, for example the methyl ether of isobutanol. Acrylic acid can also be obtained by oxidation of acrolein under gas phase catalysis. Methacrylic acid can also be obtained by oxidation of methacrolein under gas phase catalysis.

In the context of such preparation processes, it is normal to obtain product gas mixtures from which the (meth)acrylic acid and/or the (meth)acrolein have to be removed.

Esters of (meth)acrylic acid are obtainable, for example, by direct reaction of (meth)acrylic acid and/or (meth)acrolein with the appropriate alcohols. However, in this case too, product mixtures are at first obtained, from which the (meth)acrylic esters have to be removed.

The separation columns in which these separation processes are conducted comprise separating internals. In the thermal separation processes, these have the purpose of increasing the surface area for the heat and mass transfer which brings about the separation in the separation column ("the transfer area").

Useful internals of this kind include, for example, structured packings, random packings and/or trays, which are also referred to as mass transfer trays. Frequently, separation columns used are those which comprise at least one sequence of mass transfer trays at least as a portion of the separating internals.

The purpose of mass transfer trays is to provide areas having essentially continuous liquid phases in the separation column in the form of liquid layers that form thereon. The surface of the vapor and/or gas stream which ascends within the liquid layer and is distributed in the liquid phase is then the crucial transfer area.

A sequence of mass transfer trays is understood to mean a sequence (a succession) of at least two mass transfer trays generally of the same design (i.e. identical), arranged one above another in the separation column. Advantageously for application purposes, the clear distance between two immediately successive mass transfer trays in such a series (sequence) of mass transfer trays is uniform (meaning that the mass transfer trays are arranged equidistantly one above another in the separation column).

The simplest embodiment of a mass transfer tray is called a trickle sieve tray. This comprises a plate, or plate segments joined to form a plate, having essentially planar passage orifices, for example round holes and/or slots, for the ascending gas or vapor phase (the terms "gaseous" and "vaporous" are used synonymously in this document) distributed over the plate (cf., for example, DE 10230219 A1, EP 1279429 A1, U.S. Pat. No. 3,988,213 and EP 1029573 A1). Any orifices beyond these (for example at least one downcomer (at least one drain segment)) are generally not present in trickle sieve trays. As a result of this absence of downcomers, both the gas ascending within the separation column (the vapor ascending within the separation column) and the liquid descending within the separation column have to move, flowing in opposite directions, alternating in time, through the (same) passage orifices (through the open cross sections of the passages). Reference is also made to the "dual flow" of ascending gas and descending liquid through the passage orifices, which is the reason why the present document also uses the term "dual-flow trays" or "dual-flow mass transfer trays" for mass transfer trays of this type.

The cross section of the passage orifices of a dual-flow tray is matched in a manner known per se to the load thereon. If the cross section is too small, the ascending gas passes through the passage orifices at such a high velocity that the liquid descending within the separation column is entrained essentially without separating action. If the cross section of the passage orifices is too great, ascending gas and descending liquid move past one another essentially without exchange, and the mass transfer tray is at risk of running dry.

In other words, the separation-active working range of a trickle sieve tray (dual-flow tray) has two limits. There has to be a minimum limiting velocity of the ascending gas, in order that a certain liquid layer is held on the trickle sieve tray, in order to enable separation-active working of the trickle sieve tray. The upper limit in the velocity of the ascending gas is fixed by the flood point, when the gas velocity leads to backup of the liquid on the trickle sieve tray and prevents it from trickling through.

The longest dimension of the passage orifices of an industrial dual-flow tray (=longest direct line connecting two points on the outline of the passage orifice cross section) is typically 10 to 80 mm (cf., for example, DE 10156988 A1). Normally, the passage orifices are identical within a trickle sieve tray (in other words, they all have the same geometric shape and the same cross section (the same cross-sectional area)). Appropriately in application terms, the circumference lines of the cross-sectional areas thereof are circles. In other words, preferred passage orifices of trickle sieve trays are circular holes. The relative arrangement of the passage orifices of a trickle sieve tray advantageously follows a strict triangular pitch (cf., for example, DE 10230219 A1). It is of course also possible for the passage orifices to be configured differently within one and the same trickle sieve tray, for example to vary over the trickle sieve tray.

Advantageously in application terms, a sequence of trickle sieve trays comprises trickle sieve trays of the same design (identical trickle sieve trays) in a separation column, preferably arranged equidistantly one above another.

According to DE 10156988 A1, it is also possible to employ sequences of trickle sieve trays in separation columns having a uniform (preferably circular) cross section within a dual-flow tray, but varying within the sequence (for example decreasing from the bottom upward).

In general, each dual-flow tray in a corresponding tray sequence concludes flush with the wall of the separation column. However, there are also embodiments in which an intermediate space interrupted only partly by bridges exists between the column wall and tray. Aside from the actual passage orifices, a trickle sieve tray typically has, at most, orifices which serve to secure the tray on support rings or the like (cf., for example, DE 10159823 A1).

Within the normal working range of a sequence of trickle sieve trays, the liquid descending within the separation column trickles downward in droplets from dual-flow tray to dual-flow tray, meaning that the gas phase ascending between the dual-flow trays is permeated by a divided liquid phase. Some of the droplets that hit the lower trickle sieve tray in each case are atomized. The gas stream flowing through the passage orifices bubbles through the liquid layer formed on the surface of the tray, with intense heat and mass transfer between the liquid and the gas.

According to the gas and liquid load, there is a tendency in trickle sieve trays, in the case of column diameters of >2 m, for slightly unequal distributions of liquids to build up, and thus for the liquid hold-up of a tray to vary over a large area or for a circulating wave to form, which can firstly adversely affect the mechanical stability of the column body and secondly reduces the separating action, since the liquid distribution under these conditions is then time-dependent and highly location-dependent. To avoid such non-steady states, it has therefore been found to be advantageous to distribute baffles in the form of vertical metal sheets over the tray cross section, which prevent or at least greatly reduce buildup of liquid within the column body. The height of the metal sheets should correspond approximately to the height of the liquid froth layer that forms. This is about 20 cm at customary loads.

The circumference line of the cross section of a separation column is generally circular. This applies correspondingly to the accompanying mass transfer trays.

Dual-flow trays usable for the purposes of this document are described, for example, in Technische Fortschrittsberichte [Technical Progress Reports], vol. 61, Grundlagen der Dimensionierung von Kolonnenböden [Fundamentals of the Dimensioning of Column Trays], pages 198 to 211, Verlag Theodor Steinkopf, Dresden (1967) and in DE 10230219 A1.

In the case of columns of high diameter, it has been found that a deterioration in the separating action arises between gas introduced at the bottom and liquid dripping downward from the top.

It is therefore an object of the present invention to specify a column and a process for thermal treatment of fluid mixtures in which the separating action is improved.

This object is achieved in accordance with the invention by a column having the features of claim 1 and a process having the features of claim 13. Advantageous configurations and developments are apparent from the dependent claims.

It is thus a characteristic feature of the column of the invention that a gas distribution tray which is disposed between the lowermost of the sequence of dual-flow mass transfer trays and the gas entry orifice has orifices for vertical passage of gas which can be introduced into the column cavity via the gas entry orifice, the orifices being formed so as to bring about equal gas distribution over the column cross section.

It has been found in accordance with the invention that the deterioration in the separating action in the case of conventional columns having dual-flow mass transfer trays, particularly in the case of columns of high diameter, is caused by the gas introduced being distributed inhomogeneously over the cross-sectional area of the column beneath the lowermost dual-flow mass transfer tray. Inhomogeneities arise especially with regard to the pressure distribution of the gas over the cross-sectional area of the column. In many cases, the gas pressure in the outer region is higher than in the middle. This has the adverse consequence that a greater amount of gas flows upward through the outer orifices of the lowermost dual-flow mass transfer tray than through the orifices in the region in the middle of the dual-flow mass transfer tray. The result of this inhomogeneous gas flow upward through the orifices of the dual-flow mass transfer tray is that the separating action of the column deteriorates.

The spatial terms "above", "below", "horizontal" and "vertical" relate, unless explicitly mentioned otherwise, to the orientation of the column during operation.

The effect of the inventive disposal of a gas distribution tray between the lowermost dual-flow mass transfer tray and the gas entry orifice is that equal gas distribution arises over the column cross section between the gas distribution tray and the lowermost dual-flow mass transfer tray, especially immediately below the lowermost dual-flow mass transfer tray. This in turn has the consequence that essentially the same amount of gas flows through each of the equally sized orifices in the lowermost dual-flow mass transfer tray. This equal gas distribution also continues to dual-flow mass transfer trays disposed higher up, such that an equal gas distribution is achieved overall over the column cross section in the region of the dual-flow mass transfer trays. This in turn has the effect of an improved separating action between the ascending gas and the descending liquid.

In one configuration of the column of the invention, the gas entry orifice and the gas distribution tray are configured such that the dynamic pressure of the gas flowing into the column cavity is $\frac{1}{6}$ to $\frac{1}{10}$, especially $\frac{1}{7}$ to $\frac{1}{10}$, of the pressure drop of the gas distribution tray. The dynamic pressure of the gas flowing into the column cavity is especially $\frac{1}{6}$ to $\frac{1}{10}$ of the dry pressure drop of the gas distribution tray.

The dynamic pressure of the gas flowing into the column cavity is understood in this document especially to mean the backpressure at the gas entry orifice.

The dry pressure drop of a tray is understood in this document to mean the pressure drop without contact of liquid with the tray.

The pressure drop that a gas distribution tray has to achieve in order to assure a homogeneous gas distribution depends especially on the extent of the inhomogeneities upstream of the gas distribution tray. The dry pressure drop of the gas distribution tray has to be sufficiently high to bring about equal gas distribution over the column cross section. The dry pressure drop is especially relevant here, since a tray with inhomogeneous incoming flow towards the tray has a tendency to allow the gas through on one horizontal side and to allow the liquid to trickle through on another horizontal side without contact of the gas with the liquid again. If, therefore, the inhomogeneous incoming flow toward the tray results in separation of the passage regions for gas and liquid, the tray has to be capable, by virtue of its dry pressure drop, of smoothing out the flow again, i.e. of eliminating the separation of the passage regions for gas and liquid again. It has been found in accordance with the invention that, for homogeneous gas distribution, the pressure drop of the gas distribution tray should be in the region of 6 to 10 times, especially 7 to 10 times, the dynamic pressure of the gas at the gas entry orifice, i.e. especially in the inflow stub. This is also true when the gas distribution tray is not a dual-flow mass transfer tray. If, for example, the backpressure at the gas entry orifice is about 240 Pa or 2.4 mbar, the pressure drop of the flow rectifier, i.e. of the gas distribution tray, should be at least 14 mbar, especially at least 17 mbar.

In one configuration of the column of the invention, the orifices of the gas distribution tray are arranged in uniform distribution over the cross section. For example, the centers of the orifices of the gas distribution tray are arranged on at least two concentric circles. Preferably, the gas distribution tray has a 0.2 to 1 orifice per square meter. This achieves the effect that particularly good equality of gas distribution is brought about over the column cross section.

In one configuration of the column of the invention, the proportion of the orifice area formed by the orifices of the gas distribution tray relative to the inner cross-sectional area of the column is within a range from 10% to 20%.

In one configuration of the column of the invention, the proportion of the orifice area formed by the orifices at least of the lowermost of the sequence of dual-flow mass transfer trays relative to the inner cross-sectional area of the column is greater than this proportion for the gas distribution tray. The proportion is in particular within a range from 14% to 20%. The dry pressure drop of this lowermost of the sequence of dual-flow mass transfer trays is, for example, within a range from 0.5 to 1.0 mbar.

Inhomogeneities with regard to the pressure distribution of the gas over the cross-sectional area of a column are balanced out most efficiently if the equality of gas distribution over the column cross section is reached already below the gas distribution tray. Such inhomogenieties cause the problems discussed above. In many cases, the gas pressure in the outer region is higher than in the middle, in particular when the gas is fed close to the wall of the column. This has the adverse consequence that a greater amount of gas flows upward through the outer orifices of the lowermost dual-flow mass transfer tray than through the orifices in the region in the middle of the dual-flow mass transfer tray. On the contrary, when the gas is fed to the center of the column, i.e. to the middle, the pressure in the outer region, i.e. close to the wall, will be lower than in the middle. This has the adverse consequence that a smaller amount of gas flows upward through the outer orifices of the lowermost dual-flow mass transfer tray than through the orifices in the region in the middle of the dual-flow mass transfer tray. The result of this inhomogeneous gas flow upward through the orifices of the dual-flow mass transfer tray is that the separating action of the column deteriorates. These problems arise to a lesser extent also when the flow resistance for vertical passage of the gas through the gas distribution tray is too small when compared to the flow resistance for vertical passage of the gas through the lowermost dual-flow mass transfer tray. Equal gas distribution would then be brought about in part only under the lowermost dual-flow mass transfer tray. However, as liquid flows downward through the orifices of this dual-flow mass transfer tray, the discussed inhomogenieties would establish instead with the consequence of deterioration of separating action, though to a lesser extent than without gas distribution tray.

The ratio of the flow resistances can, for example, be controlled via the orifice ratios of both trays.

In a preferred configuration of the column of to the invention, the proportion of the orifice area formed by the orifices at least of the lowermost of the sequence of dual-flow mass transfer trays relative to the inner cross-sectional area of the column is therefore at least 1.13 times larger, in general at least 1.16 times larger, preferably at least 1.20 times larger, more preferably at least 1.25 times larger, e.g at least 1.30 times larger, in particular at least 1.35 times larger, than the same proportion of the gas distribution tray.

Both trays are preferably designed such that the pressure drop of the gas distribution tray, especially the dry pressure drop of the gas distribution tray, is at least 20%, preferably at least 50%, in particular at least 150%, preferably at least 200%, more preferably at least 300%, e.g. at least 400% of the pressure drop of the lowermost dual-flow mass transfer tray, especially the dry pressure drop of the lowermost dual-flow mass transfer tray, of the sequence of dual-flow mass transfer trays.

The person skilled in the art knows which orifice areas should be chosen and which relative pressure drops of the gas distribution tray and of the lowermost dual-flow mass transfer tray should be established in view of specific expected conditions of a particular process. The pressure of the gas that is fed into the column through the gas entry orifice may vary, for example, when an upstream process is impaired. As a consequence, temporal inhomogenieties which further deteriorate the separating action of the column may arise in addition to the spacial inhomogeneities discussed in other sections of this document. It is advantageous to establish not only spacially but also temporally equal gas distribution. The spacially equal gas distribution should also be reached to a large extent under the gas distribution try and not or only to a minor extent under the lowermost dual-flow mass transfer tray. In particular when only minor variations of the pressure of the gas being fed into the column through the gas entry orifice are to be expected, it may be sufficient when the pressure drop of the gas distribution tray (9) is at least 20% of the pressure drop of the lowermost dual-flow mass transfer tray, in particular of the dry pressure drop of the lowermost dual-flow mass transfer tray, of the sequence of dual-flow mass transfer trays. Small spacial and temporal inhomogenieties are then balanced to a sufficient extent. In particular when strong variations of the pressure of the gas being fed into the column through the gas entry orifice are to be expected, it may be necessary that the pressure drop of the gas distribution tray is higher than the pressure drop of the lowermost dual-flow mass transfer tray. It may then be necessary that the pressure drop of the gas distribution tray (9) is, for example, at least 400% of the pressure drop of the lowermost dual-flow mass transfer tray, especially the dry pressure drop of the lowermost dual-flow mass transfer tray, of the sequence of dual-flow mass transfer trays.

In general, both trays are designed such that the pressure drop of the gas distribution tray, especially the dry pressure drop of the gas distribution tray, is at most 5 000% (e.g. 400% to 5 000%), preferably at most 3 000% (e.g. 300% to 3 000%), in particular at most 2 000% (e.g. 200% to 2 000%), preferably at most 1 000% (e.g. 150% to 1 000%) of the lowermost dual-flow mass transfer tray, especially the dry pressure drop of the lowermost dual-flow mass transfer tray, of the sequence of dual-flow mass transfer trays. High pressure drops require more energy.

In one configuration of the column of the invention, the gas entry orifice in the column is aligned such that gas entering the column cavity forms a horizontal vortex. In the case of such a configuration of the gas entry orifice, the risk of inhomogeneous gas distribution over the horizontal cross section of the column is particularly high. If, for example, the gas flows tangentially into the column cavity, the gas pressure in the outer region is typically higher than in the middle. This inhomogeneous pressure distribution is balanced out by the inventive disposal of the gas distribution tray, such that there is a homogeneous gas pressure distribution below the lowermost dual-flow mass transfer tray.

In a further configuration of the column of the invention, a liquid draw disposed above the gas distribution tray or in the gas distribution tray has an inlet for liquid from an upper collecting area of the gas distribution tray and an outlet in a region beneath the gas distribution tray. The gas distribution tray may thus especially be a mass transfer tray with forced liquid conduction. This liquid draw prevents liquid from flowing downward through the same orifices through which the gas flows upward. The gas distribution tray is thus not a dual-flow tray, since the liquid does not flow downward through the same orifices through which the gas flows upward. In this way, very controlled upward flow of the gas through the gas distribution tray is achieved, and the gas passage rate, the pressure drop achieved by the gas distribution tray and the equal distribution of the gas pressure above the gas distribution tray brought about as a result are determined by the size, geometry and arrangement of the orifices in the gas distribution tray for the gas flowing upward.

Advantageously, a collecting tank for the liquid flowing through the liquid draw disposed between the inlet and the outlet of the liquid draw may be arranged such that the liquid collecting in the collecting tank provides a hydraulic seal. This hydraulic seal prevents formation of a bypass for the ascending gas. The ascending gas cannot flow upward through the liquid draw past the orifices of the gas distribution tray.

The liquid draw may especially comprise a pipe in siphon-like form which forms the collecting tank. This pipe in siphon-like form provides a hydraulic seal for the ascending gas in a simple manner.

In a further configuration, the inlet of the liquid draw comprises an orifice in the upper collecting area of the gas distribution tray. From this orifice, a drainpipe extends downward. The collecting tank in this case may take the form of a collecting cup disposed beneath the lower orifice of the drainpipe, the drainpipe passing through an area of the collecting cup which is formed by the upper edge of the collecting cup, and the upper edge of the collecting cup being disposed above the lower edge of the lower orifice of the drainpipe. The area formed by the upper edge of the collecting cup is just a theoretical area. It especially coincides with the liquid surface when the collecting cup is filled with liquid. Thus, when the collecting cup is filled with liquid, the drainpipe dips into the liquid present in the collecting cup, such that the hydraulic seal is provided in this way.

In order that the liquid that collects on the collecting area of the gas distribution tray flows away via the liquid draw, the collecting area may have a slope in the direction of the inlet for the liquid draw. For example, it is also possible for a channel provided in the collecting area to have a slope and open into the inlet of the liquid draw.

In a further configuration of the column of the invention, the gas distribution tray is a chimney tray having a chimney having a covering hood. The chimney tray especially comprises several chimneys which provide the orifices of the gas distribution tray for the gas passage from the bottom upward. The covering hoods of the chimneys prevent the liquid which trickles from the top downward from passing downward through the chimneys. Instead, the liquid trickling downward collects on the collecting area of the chimney tray. From there, it is conducted downward as described above through the liquid draw into the region beneath the gas distribution tray.

The clear distance between two immediately successive dual-flow mass transfer trays within the column of the invention is especially not more than 700 mm, preferably not more than 600 mm or not more than 500 mm. Appropriately in application terms, the clear distance within the tray sequence is 300 to 500 mm. In general, the tray separation should not be less than 250 mm.

The height of the column body is, for example, greater than 5 m, especially greater than 10 m. However, it is also possible for the height of the column body to exceed 30 m or 40 m.

Further separating internals may be disposed between the dual-flow mass transfer trays. The separating internals improve the mass separation in the separation column. These further internals may be provided, for example, in the form of packings, especially structured or ordered packings, and/or beds of random packings. Among the random packings, preference is given to those comprising rings, helices, saddles, Raschig, Intos or Pall rings, Berl or Intalox saddles, Top-Pak etc. Structured packings particularly suitable for extraction columns for use in accordance with the invention are, for example, structured packings from Julius Montz GmbH in 0-40705 Hilden, for example the Montz-Pak B1-350 structured packing. Preference is given to using perforated structured packings made from stainless steel sheets. Packed columns having ordered packings are known per se to those skilled in the art and are described, for example, in Chem.-Ing. Tech. 58 (1986) no. 1, pages 19-31 and in the Technische Rundschau Sulzer February 1979, pages 49 ff. from Gebrüder Sulzer Aktiengesellschaft in Winterthur, Switzerland.

The invention further relates to a thermal separation process between at least one gas ascending within a column as described above and at least one liquid descending within the column.

The invention thus relates to a process for thermal treatment of fluid mixtures in a column having a cylindrical, vertically aligned column body which forms a column cavity in which a sequence of vertically spaced-apart dual-flow mass transfer trays is mounted, having at least one gas entry orifice disposed below the lowermost of the sequence of dual-flow mass transfer trays, and having a gas distribution tray which is disposed between the lowermost of the sequence of dual-flow mass transfer trays and the gas entry orifice and has orifices for vertical passage of gas. In the process of the invention, liquid is introduced into an upper region of the column and this liquid descends within the column. In addition, gas is introduced into the column cavity through the gas entry orifice. This gas flows upward through the orifices of the gas distribution tray, giving rise to a pressure drop, the orifices being formed so as to bring about equal gas distribution over the column cross section.

Since the process of the invention can especially be executed with the column described above, it also has the same advantages as this column.

In the process of the invention, the dynamic pressure of the gas flowing into the column cavity is especially ⅙ to 1/10, preferably 1/7 to 1/10, of the pressure drop, especially the dry pressure drop, of the gas distribution tray.

In the process of the invention, the ascending gas and/or the descending liquid especially comprises (meth)acrylic monomers.

The thermal separation process of the invention may, for example, be a process for fractional condensation for separation of acrylic acid from a product gas mixture comprising acrylic acid from a heterogeneously catalyzed gas phase partial oxidation of a C3 precursor compound (especially propene and/or propane) of the acrylic acid with molecular oxygen to give acrylic acid.

There follows an elucidation of working examples of the column of the invention and working examples of the process of the invention with reference to the drawings.

The working example described hereinafter relates to a separation column 1 as used, for example, in a process for fractional condensation for separation of acrylic acid from a product gas mixture comprising acrylic acid from a heterogeneously catalyzed gas phase partial oxidation of a C3 precursor compound (especially propene and/or propane) of the acrylic acid with molecular oxygen to give acrylic acid.

Figure 1:
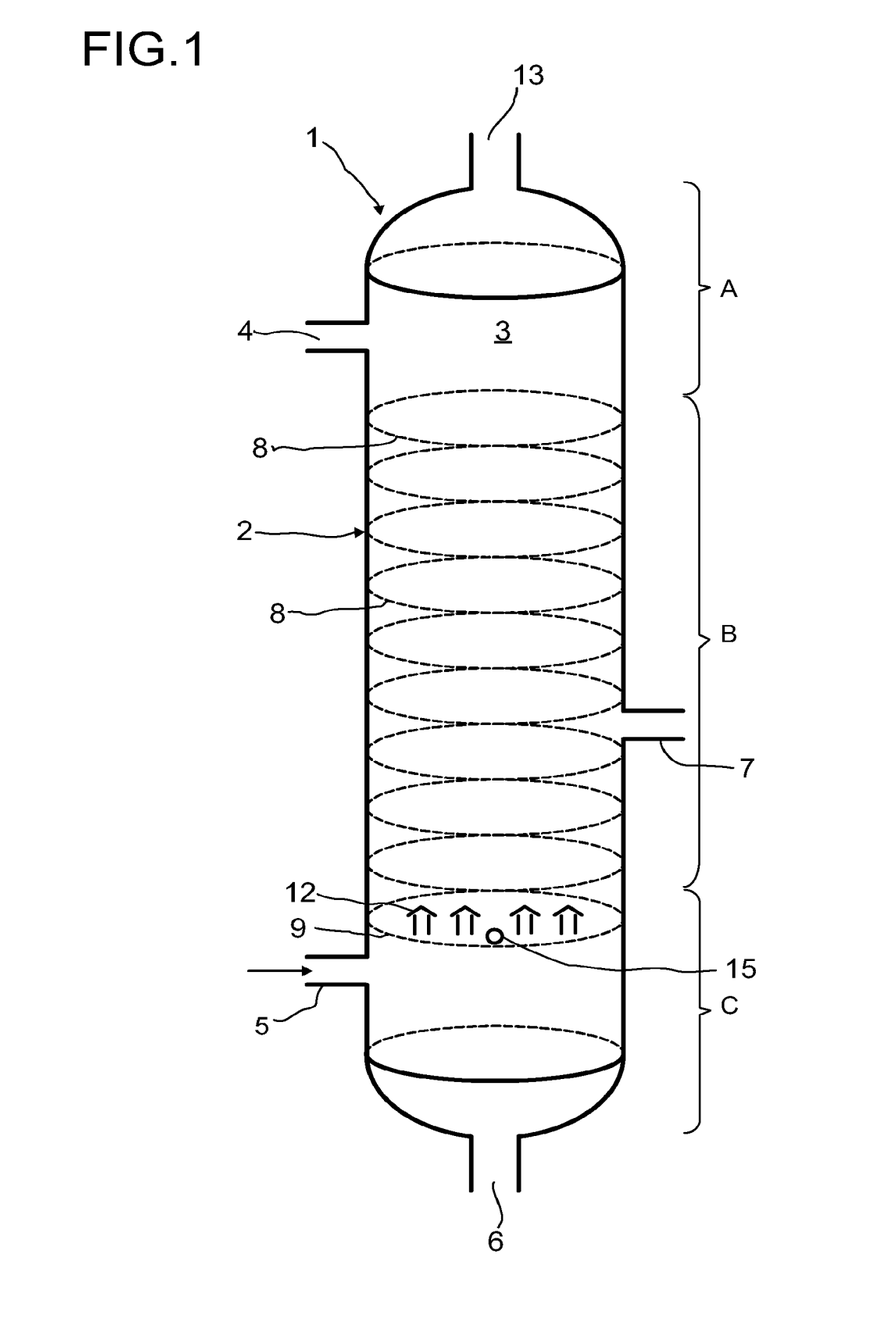
FIG. 1 shows a schematic view of a column in one working example of the invention.

FIG. 1 shows the separation column 1 known per se in schematic form. It comprises a cylindrical column body 2, the axis of which is aligned vertically. The column body 2 is essentially a hollow cylinder. This means that the column body 2 forms a column cavity 3. The column body 2 is manufactured from stainless steel. On the outside, the separation column 1 is normally thermally insulated in a conventional manner. The height of the separation column 1 is 40 m. The internal diameter of the column body 2 is 7.4 m throughout.

In the vertical direction, the separation column 1 is divided into three regions: the upper region A is referred to as the column head. At the column head is provided a feed 4 through which a liquid can be introduced into the column cavity 3. In addition, an offgas line 13 for withdrawal of the gaseous mixture is formed at the top.

Beneath the column head, a region B is formed. In this region, the fractional condensation is conducted. In the region B, a sequence of vertically spaced-apart dual-flow trays 8 is secured in the column cavity 3. These dual-flow trays 8 serve for mass transfer. They are thus mass transfer trays. They have a multitude of orifices for passage of liquid and gas in countercurrent.

The orifices of the dual-flow trays 8 are circular and have a uniform diameter of 14 mm, with the punching burr pointing downward in the separation column. The orifice ratio, i.e. the proportion of the orifice area formed by the orifices relative to the inner cross-sectional area of the column 1 or of the dual-flow tray 8, is 19.75%. The arrangement of the centers of the circular orifices follows a strict triangular pitch. The closest distance between the centers of two circles is 30 mm.

In the case of such a geometry of the orifices, the pressure drop of the dual-flow trays 8 is so low that the inhomogeneous gas pressure distribution which arises when the gas flows in through the gas entry orifice 5 cannot be balanced out. The dry pressure drop of the dual-flow trays 8 of the present working example is 4 mbar for each of the trays 8.

Also disposed within the region B is a withdrawal line 7 through which crude acrylic acid is withdrawn.

Figure 2:
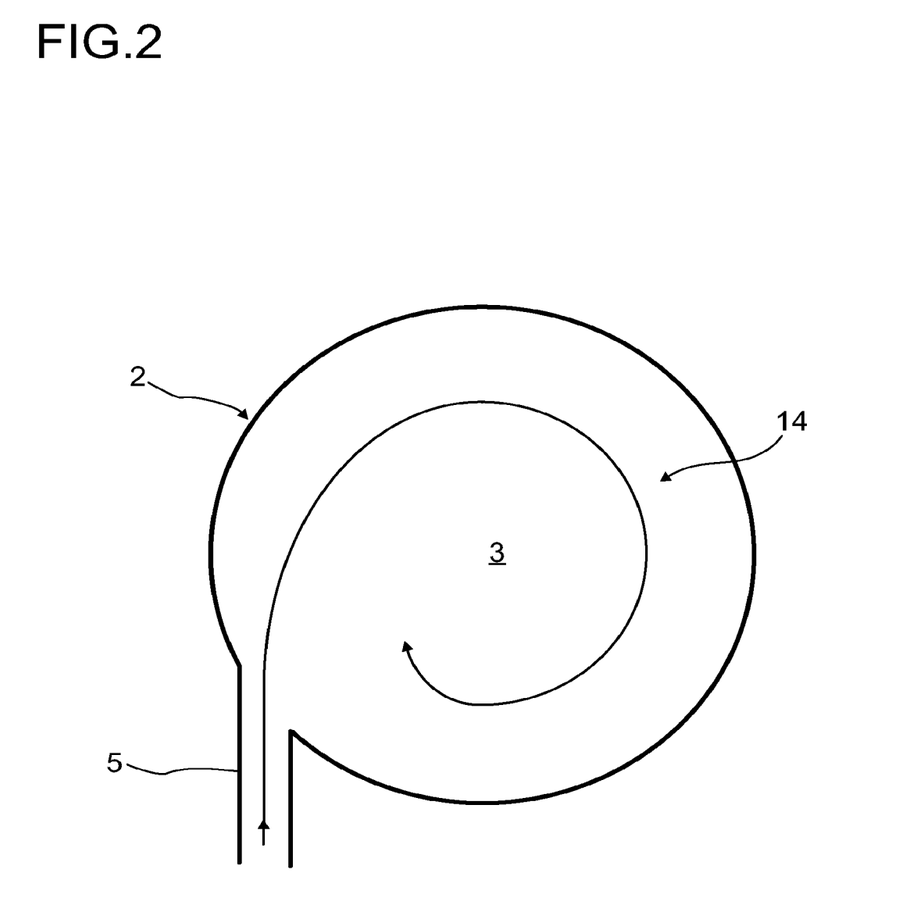
FIG. 2 shows a cross section of the column shown in FIG. 1 in the region of the gas inlet.

Beneath the region B, the column bottom is formed in the region C. In the column bottom, there is a gas entry orifice 5 for tangential introduction of gas into the column cavity 3. The introduction of gas is shown in detail in FIG. 2. Through the gas entry orifice 5, the gas enters the column cavity 3 in a tangential manner and forms a horizontal vortex 14 therein. Since the diameter of the column 1 is relatively large, it may be the case here that the gas pressure in the outer region is greater than in the middle of the column cavity 3.

Again with reference to FIG. 1, there is also an outlet 6 for the bottoms liquid in the column bottom. The liquid pumped away may be fed, for example, to a spray apparatus (quench). In the spray apparatus, the liquid sprayed is supplied with gas. Thereafter, the gas passes through the gas entry orifice 5 into the column 1.

According to the invention, a gas distribution tray 9 in the form of a chimney tray is disposed beneath the lowermost dual-flow tray 8 but above the gas entry orifice 5, i.e. between the lowermost dual-flow tray 8 and the gas entry orifice 5. The gas distribution tray 9, in the case of the chimneys, has 11 orifices for vertical passage of gas which has been introduced into the column cavity 3 via the gas entry orifice 5. The size, geometry and number of these orifices are such that equal gas distribution over the column cross section beneath the lowermost dual-flow tray 8 is brought about.

Equal gas distribution in this document is understood to mean that the dynamic pressure of the gas flowing into the column cavity 3 is $\frac{1}{6}$ to $\frac{1}{10}$ of the pressure drop, especially the dry pressure drop, of the gas distribution tray 9. In this case, the pressure drop of the gas distribution tray 9 is sufficiently high to bring about equal gas distribution over the column cross section. If, for example, the backpressure at the gas entry orifice is about 2.4 mbar, the dry pressure drop of the gas distribution tray 9 is, for example, 17 mbar.

In addition, the gas distribution tray 9 has a liquid draw 15. Through this liquid draw, the liquid which collects in the gas distribution tray 9 is guided into the column bottom.

Figure 3:
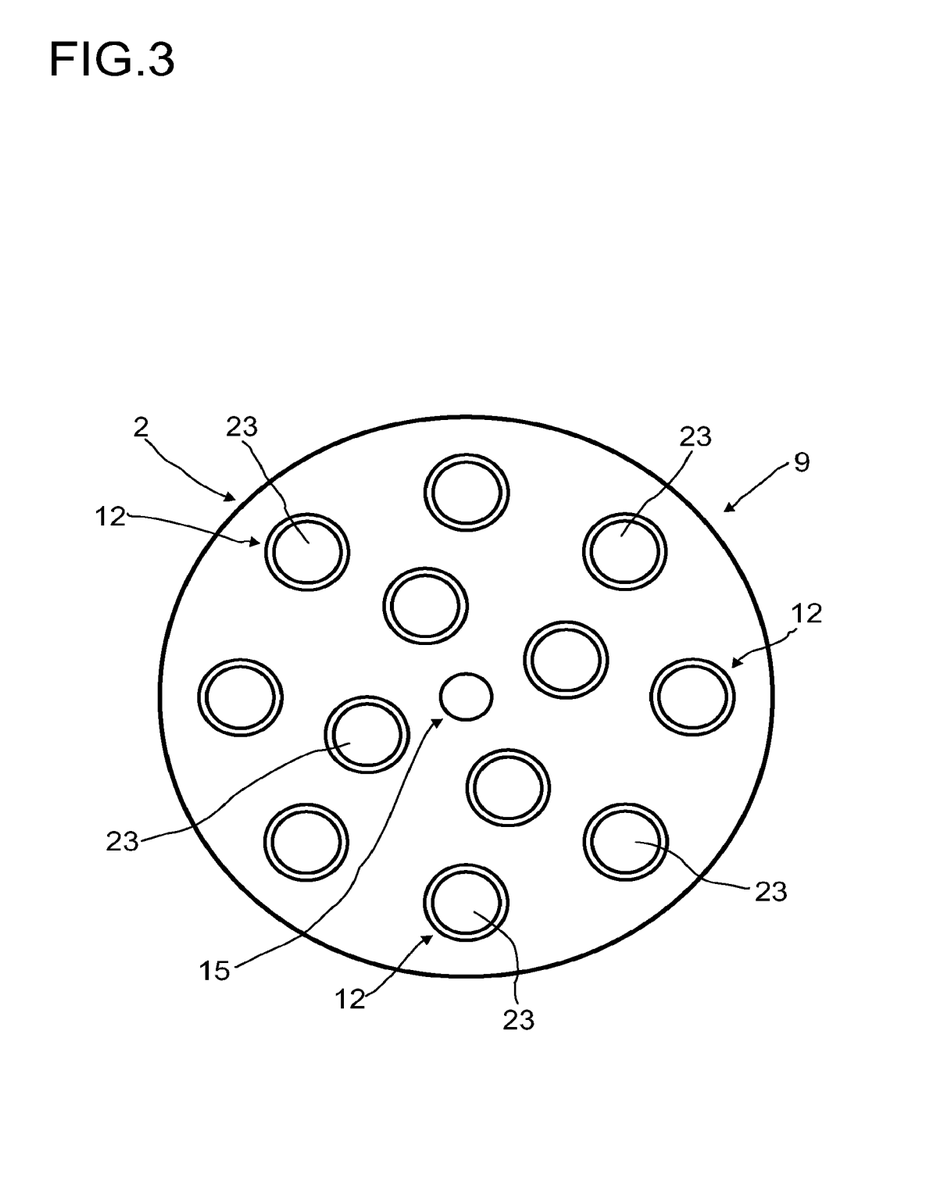
FIG. 3 shows a cross section of the column shown in FIG. 1 in the region of the gas distribution tray.
Figure 4:
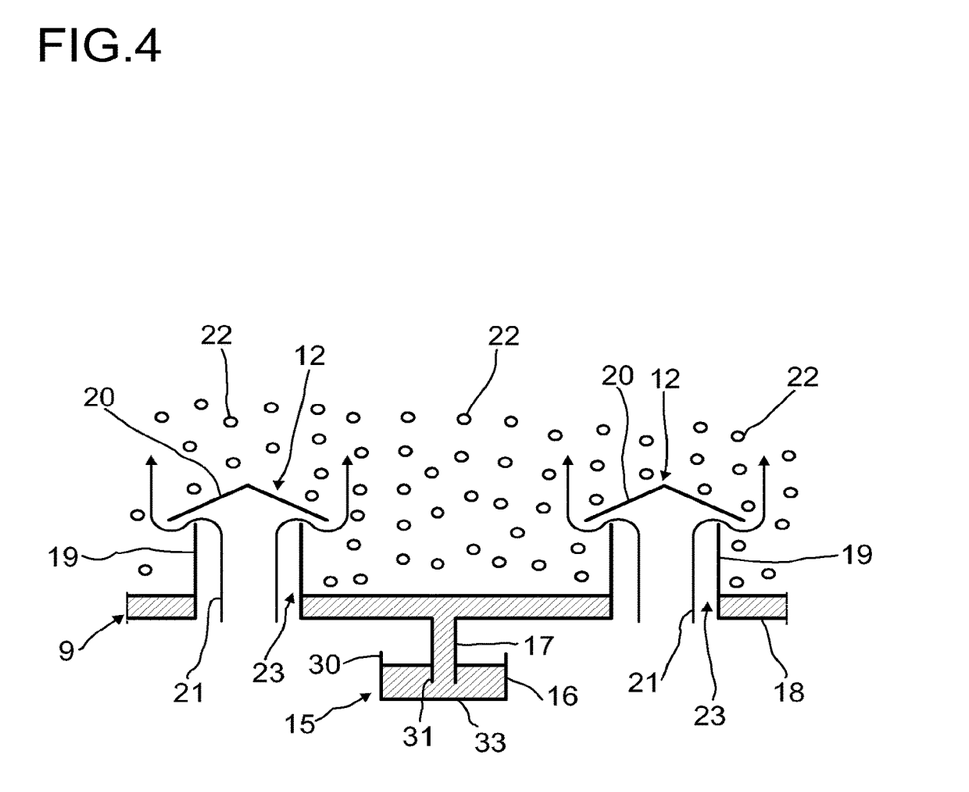
FIG. 4 shows a detail of a cross section of the gas distribution tray shown in FIG. 3

With reference to FIGS. 3 and 4, details of the gas distribution tray are elucidated:

The gas distribution tray 9 has a diameter of 7.4 m, such that it can be secured horizontally in the column interior 3 on the column body 2. In addition, the gas distribution tray 9 has a total of twelve chimneys 12 which form orifices 23 for vertical passage of gas in the upward direction. The orifices 23 have a circular area and a diameter of 810 mm. The orifice ratio, i.e. the proportion of the area formed by the orifices 23 in the total area of the gas distribution tray 9 is thus 14.38%. The orifice ratio of the lowermost dual-flow mass transfer tray 8 is 19.75% which is 1.37 times larger than that of the gas distribution tray 9.

The orifices 23 are distributed over the gas distribution tray 9 in such a way that the centers of eight orifices 23 are arranged in homogeneous distribution on a first outer circular ring which is concentric with respect to the column body 2, and the centers of four orifices 23 are arranged in homogeneous distribution on an inner circular ring which is also concentric with respect to the outer circular ring and to the column body 2. Two adjacent orifices 23 on the outer circular ring together with one orifice 23 on the inner circular ring form an equilateral triangle, and so a total of four equilateral triangles are formed. The orifices 23 are thus arranged in homogeneous distribution over the cross section of the gas distribution tray 9.

For each of the orifices 23, a cylindrical body or chimney body 19 extends upward from a collecting area 18 of the gas distribution tray 9. Above the chimney body 19, spaced apart in the vertical direction, is a covering hood 20 which fully covers the orifice 23 and extends over the chimney body 19 in the horizontal direction. The covering hood 20 prevents the liquid droplets 22 trickling down from being able to pass through the orifice 23 through the gas distribution tray 9.

In the middle of the gas distribution tray 9 is disposed a liquid draw 15. The liquid draw 15 comprises a circular orifice, from which a drainpipe 17 extends downward. Through the drainpipe 17, liquid which collects in the collecting area 18 of the gas distribution tray 9 can drain off downward. For this purpose, the collecting area 18 may be inclined in the direction of the drainpipe 17. Beneath the drainpipe 17 is a collecting cup 16 which forms a collecting tank for liquid. The lower edge 31 of the lower orifice of the drainpipe 17 is spaced apart vertically from the base 33 of the collecting cup 16. In addition, the upper edge 30 of the collecting cup 16 is disposed above the lower edge 31 of the drainpipe 17. Liquid which flows downward through the drainpipe 17 into the collecting cup 16 collects therein, such that the liquid level rises up to the upper edge 30 of the collecting cup 16. Thereafter, the liquid overflows out of the collecting cup 16 over the upper edge 30 and then passes into the column bottom. In this condition, the drainpipe 17 dips into the liquid present in the collecting cup 16. The drainpipe 17 thus passes through a theoretical area of the collecting cup 16 which is formed by the upper edge 30 of the collecting cup 16. In this way, a hydraulic seal is provided, which prevents gas ascending upward from being able to pass upward through the gas distribution tray 9 through the orifice of the drainpipe 17. It is thus possible to ensure that the gas 21 rising upward only rises upward through the orifices 23 of the chimneys 12.

Figure 5:
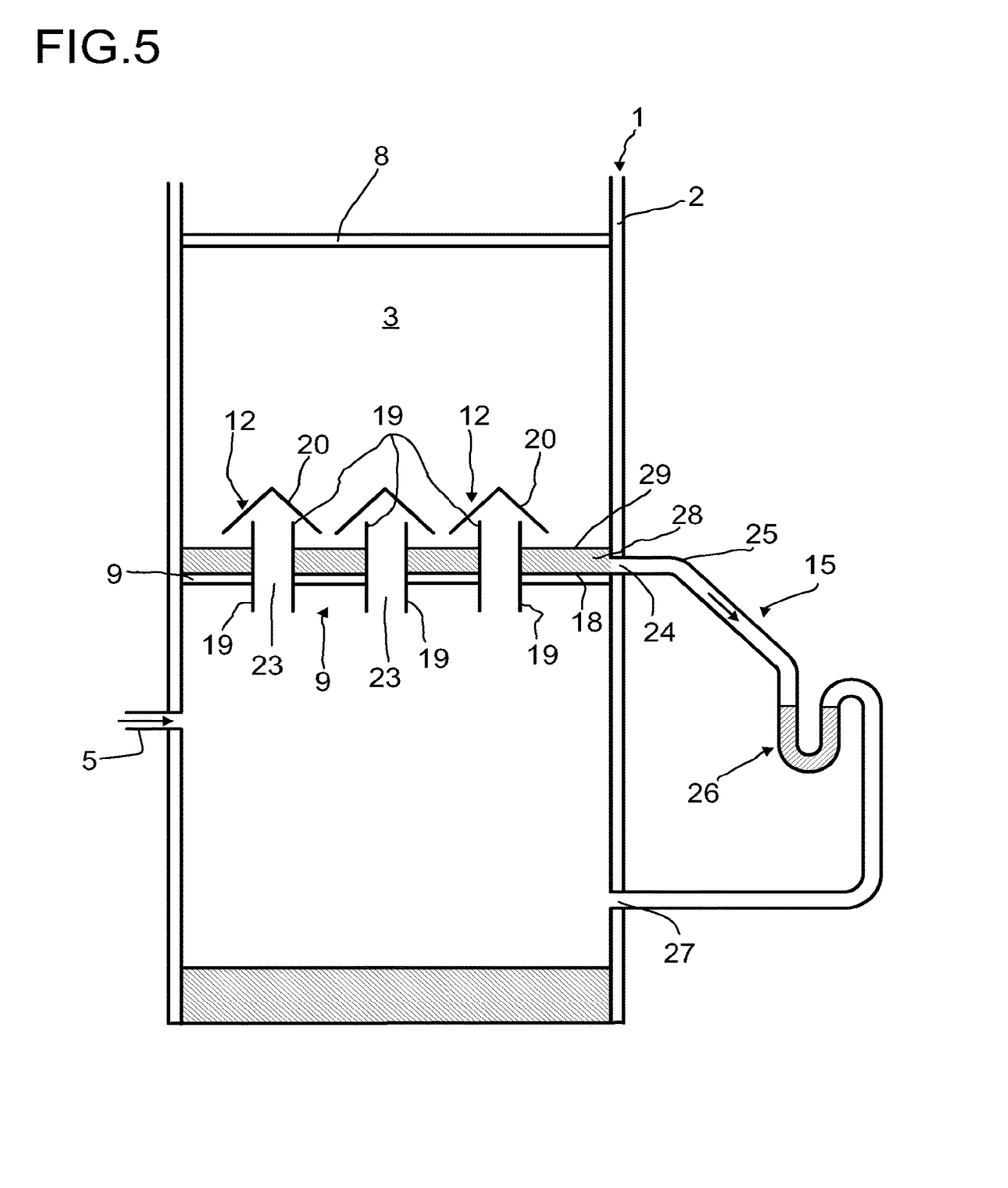
FIG. 5 shows a schematic cross section of the lower region of a further working example of the column.

FIG. 5 shows, in schematic form, another example of the liquid draw 15 having the hydraulic seal:

In this case, the gas distribution tray 9 does not have a liquid draw 15 in the middle. Instead, this liquid draw 15 is formed in the column body 2. For this purpose, an inlet 24 is provided in the column body 2 immediately above the collecting area 18 of the gas distribution tray 9. The inlet 24 is connected to a tube 25 which merges into a pipe 26 in siphon-like form. Thereafter, the pipe opens back into the column cavity 3 at an outlet 27 beneath the gas distribution tray 9. In this way, liquid 28 which collects in the collecting area 18 of the gas distribution tray 9 can be removed via the liquid draw 15 and fed to the column bottom. The inlet 24 is disposed beneath the upper edge of the chimney body 19, such that no liquid 28 can overflow the chimney body 19 and pass downward through the orifices 23.

There follows a description of a working example of the process of the invention which is executed with the above-described separation column 1 of one of the working examples.

The process is a thermal separation process between at least one gas ascending in the separation column 1 and at least one liquid descending in the separation column 1. The ascending gas and/or the descending liquid especially comprises (meth)acrylic monomers.

In the separation process, a fractional condensation for separation of acrylic acid from a product gas mixture comprising acrylic acid from a heterogeneously catalyzed gas phase partial oxidation of a C3 precursor compound (especially propene and/or propane) of the acrylic acid with molecular oxygen to give acrylic acid is conducted in a separation column 1 comprising separating internals as described above. In the process, the dynamic pressure of the gas entering the column cavity 3 is $\frac{1}{6}$ to $\frac{1}{10}$, preferably $\frac{1}{7}$ to $\frac{1}{10}$, of the pressure drop of the gas distribution tray 9. Otherwise, the process is conducted as described in documents DE 19924532 A1, DE 10243625 A1 and WO 2008/090190 A1.

The term "C3 precursor" of acrylic acid encompasses those chemical compounds which are obtainable in a formal sense by reduction of acrylic acid. Known C3 precursors of acrylic acid are, for example, propane, propene and acrolein. However, compounds such as glycerol, propionaldehyde, propionic acid or 3-hydroxypropionic acid should also be counted among these C3 precursors. Proceeding from these, the heterogeneously catalyzed gas phase partial oxidation with molecular oxygen is at least partly an oxidative dehydrogenation. In the relevant heterogeneously catalyzed gas phase partial oxidations, the C3 precursors of acrylic acid mentioned, generally diluted with inert gases, for example molecular nitrogen, CO, CO2, inert hydrocarbons and/or water vapor, are passed in a mixture with molecular oxygen at elevated temperatures and optionally elevated pressure over transition metal mixed oxide catalysts, and converted oxidatively to a product gas mixture comprising acrylic acid.

Typically, the product gas mixture comprising acrylic acid from a heterogeneously catalyzed gas phase partial oxidation of C3 precursors (e.g. propene) of the acrylic acid with molecular oxygen over catalysts in the solid state, based on the total amount of the specified constituents present (therein), has the following contents:

1% to 30% by wt. of acrylic acid,
0.05% to 10% by wt. of molecular oxygen,
1% to 30% by wt. of water,
0% to 5% by wt. of acetic acid,
0% to 3% by wt. of propionic acid,
0% to 1% by wt. of maleic acid and/or maleic anhydride,
0% to 2% by wt. of acrolein,
0% to 1% by wt. of formaldehyde,
0% to 1% by wt. of furfural,
0% to 0.5% by wt. of benzaldehyde,
0% to 1% by wt. of propene, and
as the remainder, inert gases, for example nitrogen, carbon monoxide, carbon dioxide, methane and/or propane.

The partial gas phase oxidation itself can be performed as described in the prior art. Proceeding from propene, the partial gas phase oxidation can be performed, for example, in two successive oxidation stages, as described, for example, in EP 700 714 A1 and in EP 700 893 A1. It will be appreciated, however, that it is also possible to employ the gas phase partial oxidations cited in DE 19740253 A1 and in DE 19740252 A1.

In general, the temperature of the product gas mixture leaving the partial gas phase oxidation is 150 to 350° C., frequently 200 to 300° C.

Direct cooling and/or indirect cooling cools the hot product gas mixture appropriately at first to a temperature of 100 to 180° C., before it is conducted, for the purpose of fractional condensation, into region C (the bottom) of the separation column 1. The operating pressure which exists in the separation column 1 is generally 0.5 to 5 bar, frequently 0.5 to 3 bar and in many cases 1 to 2 bar.

LIST OF REFERENCE NUMERALS 1 column, separation column
2 column body
3 column cavity
4 inlet
5 gas entry orifice
6 outlet
7 withdrawal line
8 mass transfer tray
9 gas distribution tray
11 liquid draw
12 chimneys
13 draw point
14 horizontal vortex
15 liquid draw
16 collecting cup
17 drainpipe
18 collecting area
19 cylindrical body; chimney body
20 covering hood
21 gas
22 liquid droplets
23 gas passage orifice
24 inlet
25 drainpipe
26 pipe in siphon-like form
27 outlet
28 liquid
29 liquid level
30 upper edge of collecting cup
31 lower edge of lower orifice of drainpipe
32 orifices
33 base of the collecting cup

The invention claimed is:

1. A column for thermal treatment of fluid mixtures, comprising:
   a cylindrical, vertically aligned column body which forms a column cavity;
   a sequence of vertically spaced-apart dual-flow trickle sieve trays which are mounted in the column cavity and which have orifices for passage of liquid and gas in countercurrent;
   a gas distribution tray disposed below the lowermost of the sequence of dual-flow trickle sieve trays; and
   at least one gas entry orifice disposed below the gas distribution tray;
   wherein
   the gas distribution tray has orifices for vertical passage of gas introduced into the column cavity via the at least one gas entry orifice and a liquid draw for passage of liquid below the gas distribution tray,
   the orifices for vertical passage of gas are arranged in homogeneous distribution over the cross section of the gas distribution tray,
   a pressure drop obtained by the orifices of the gas distribution tray is 6 to 10 times the dynamic pressure of the gas at the at least one gas entry orifice, and
   a ratio of the orifice area of the orifices of the lowermost of the sequence of dual-flow trickle sieve trays relative to an inner cross-sectional area of the column is at least 1.13 times larger than a ratio of the orifice area of the orifices of the gas distribution tray to the inner cross-sectional area of the column,
   so as to obtain equal gas distribution over the column cross section of the gas introduced into the column through the at least one gas entry orifice.

2. The column according to claim 1, wherein the gas distribution tray has 0.2 to 1 orifice per square meter.

3. The column according to claim 1, wherein the proportion of the orifice area formed by the orifices of the gas distribution tray relative to the inner cross-sectional area of the column is within a range from 10% to 20%.

4. The column according to claim 1, wherein the pressure drop of the gas distribution tray is at least 20% of the pressure drop of the lowermost dual-flow trickle sieve tray of the sequence of dual-flow trickle sieve trays.

5. The column according to claim 1, wherein the proportion of the orifice area formed by the orifices of at least of the lowermost of the sequence of dual-flow trickle sieve trays relative to the inner cross-sectional area of the column is within a range from 14% to 20%.

6. The column according to claim 1, wherein the at least one gas entry orifice in the column is aligned such that gas entering the column cavity forms a horizontal vortex.

7. The column according to claim 1, wherein the liquid draw disposed above the gas distribution tray or in the gas distribution tray has an inlet for liquid from an upper collecting area of the gas distribution tray and an outlet in a region beneath the gas distribution tray.

8. The column according to claim 7, wherein a collecting tank for the liquid flowing through the liquid draw disposed between the inlet and the outlet of the liquid draw is arranged such that the liquid collecting in the collecting tank provides a hydraulic seal.

9. The column according to claim 8, wherein the liquid draw comprises a pipe in siphon form which forms the collecting tank.

10. The column according to claim 7, wherein the inlet of the liquid draw comprises an orifice in the upper collecting area of the gas distribution tray, from which a drainpipe extends downward, and wherein a collecting tank is a collecting cup disposed beneath the lower orifice of the drainpipe, the drainpipe passing through an area of the collecting cup which is formed by the upper edge of the collecting cup, and the upper edge of the collecting cup being disposed above the lower edge of the lower orifice of the drainpipe, such that liquid collecting in the collecting cup forms the hydraulic seal.

11. The column according to claim 1, wherein the gas distribution tray is a chimney tray comprising a chimney having a covering hood.

12. A process for thermal treatment of fluid mixtures in a column according to claim 1, comprising:
 introducing liquid into an upper region of the column wherein the liquid descends within the column and
 introducing gas into the column cavity through the at least one gas entry orifice wherein the gas flows upward through the orifices of the gas distribution tray, giving rise to a pressure drop,
 the orifices being formed so as to bring about equal gas distribution over the column cross section.

13. The process according to claim 12, wherein the ascending gas and/or the descending liquid comprises (meth)acrylic monomers.

\* \* \* \* \*

UNITED STATES PATENT AND TRADEMARK OFFICE
CERTIFICATE OF CORRECTION

PATENT NO. : 10,493,376 B2
APPLICATION NO. : 15/382073
DATED : December 3, 2019
INVENTOR(S) : Ulrich Hammon et al.

Page 1 of 1

It is certified that error appears in the above-identified patent and that said Letters Patent is hereby corrected as shown below:

In the Specification

In Column 9, Line 21, delete "0-40705" and insert -- D-40705 --, therefor.

Signed and Sealed this
Nineteenth Day of May, 2020

Andrei Iancu
*Director of the United States Patent and Trademark Office*